United States Patent [19]

Van de Wijdeven

[11] Patent Number: 5,549,560
[45] Date of Patent: Aug. 27, 1996

[54] APPARATUS AND METHOD FOR INJECTING A PHARMACEUTICAL PREPARATION IN SOLID FORM

[76] Inventor: Gijsbertus G. P. Van de Wijdeven, Grotestraat 53, NL-5256 PA Heesbeen, Netherlands

[21] Appl. No.: 335,725

[22] PCT Filed: May 13, 1993

[86] PCT No.: PCT/NL93/00098

§ 371 Date: Jan. 9, 1995

§ 102(e) Date: Jan. 9, 1995

[87] PCT Pub. No.: WO93/23110

PCT Pub. Date: Nov. 25, 1993

[30] Foreign Application Priority Data

May 13, 1992 [NL] Netherlands ............... 92.00844

[51] Int. Cl.⁶ .................................. A61M 5/20
[52] U.S. Cl. ............... 604/130; 604/140; 604/57; 604/49
[58] Field of Search .............. 604/130–137, 604/272, 274, 256, 70, 62, 68–69, 60, 140–141, 61, 143–147, 46, 28, 51, 187, 57

[56] References Cited

U.S. PATENT DOCUMENTS

| | | |
|---|---|---|
| 3,430,626 | 3/1969 | Bergman . |
| 3,809,083 | 5/1974 | Westergaard . |
| 3,977,401 | 8/1976 | Pike . |
| 4,004,566 | 1/1977 | Fischer . |
| 4,487,602 | 12/1984 | Christensen et al. . |
| 4,771,757 | 9/1988 | Chevalier . |
| 4,861,340 | 8/1989 | Smith et al. . |
| 4,921,108 | 5/1990 | Berta . |
| 5,015,237 | 5/1991 | Kleinwolterink, Jr. et al. . |
| 5,284,479 | 2/1994 | de Jong . |
| 5,395,319 | 3/1995 | Hirsch et al. . |

FOREIGN PATENT DOCUMENTS

| | | |
|---|---|---|
| 0182682 | 5/1986 | European Pat. Off. . |
| 3419876 | 11/1985 | Germany . |
| 2174606 | 11/1986 | United Kingdom . |
| 9202310 | 2/1992 | WIPO . |

OTHER PUBLICATIONS

Section Ch, Week 8315, Derwent Publications Ltd., Londen, GB; Class B07, AN 83-36278K & S U,A,933 101 (Timoshin), dated Dec. 30, 1977.

Primary Examiner—Randall L. Green
Assistant Examiner—Perry E. Van Over
Attorney, Agent, or Firm—Banner & Allegretti, Ltd.

[57] ABSTRACT

The present invention relates to a method and a device for injecting humans and animals with a pharmaceutical preparation, wherein the preparation is held in a rigid carrier (5) and the carrier is carried through the skin into the body by means of gas pressure, and wherein during carrying of a rigid carrier (5) into the body by means of gas pressure the device with which the carrier is carried into the body is held against the body. The invention likewise relates to a device for injecting animals or humans with a pharmaceutical preparation, wherein a chamber (2) is present in which a carrier (5) containing the pharmaceutical preparation can be placed, a barrel (1) connecting onto this chamber and means for carrying the carrier by means of gas pressure through the barrel into the body for injecting, wherein means are present for blocking the use of the device when it is not pressed against a body.

16 Claims, 2 Drawing Sheets

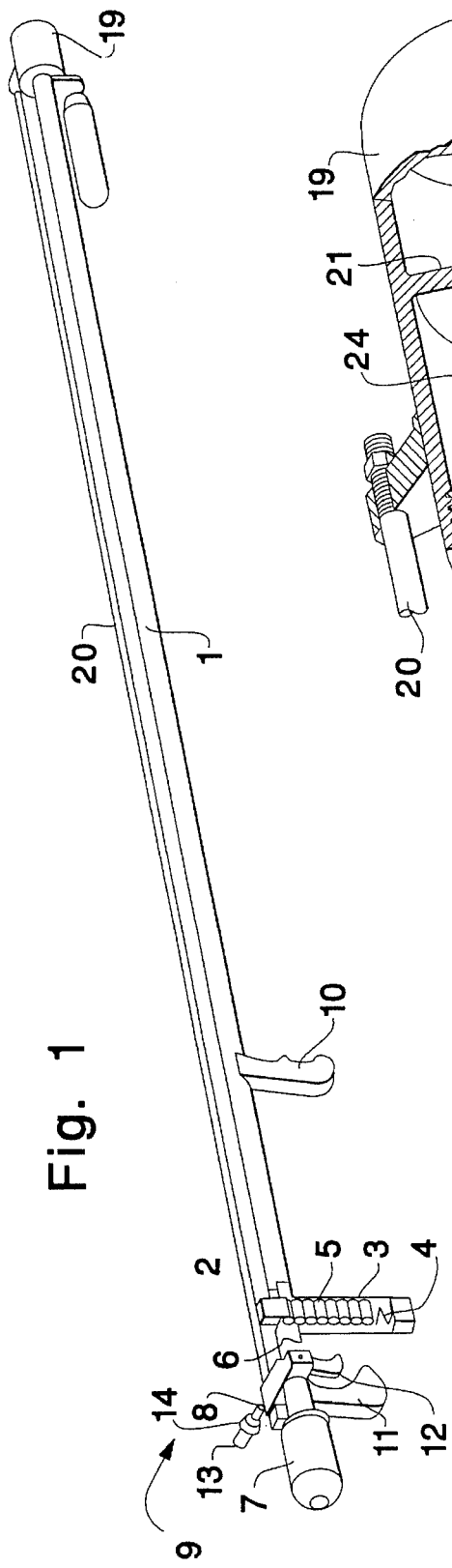

APPARATUS AND METHOD FOR INJECTING A PHARMACEUTICAL PREPARATION IN SOLID FORM

The present invention relates to a method and a device for injecting humans and animals with a pharmaceutical preparation.

Both this method and this device are generally known. Use is made herein of a syringe which is filled with the pharmaceutical preparation in liquid form, whereafter by means of a piston received in the syringe the liquid preparation is injected into the body through a needle pushed through the skin.

This method is used both with humans and with animals.

This method is however beset with the danger that the needle, after being inserted into the body, is contaminated by micro-organisms or viruses present in that body which pass onto the needle of the syringe. When the same needle is used for injecting a following body there is therefore the danger of the following body being contaminated.

While in the case of human applications it is usual to use syringes and needles for once-only use, this does result in cost increases and excessive environmental impact, particularly in the case of prophylactic inoculation on a large scale. This is the case for both human and veterinary applications.

Known from U.S. Pat. No. 4,771,757 is a method wherein the preparation is received in a rigid carrier and wherein the carrier is carried through the skin into the body by means of gas pressure.

In this method only the carrier with the pharmaceutical preparation penetrates into the body for injecting so that no instruments or parts thereof penetrate into and are removed from the body for injecting so that the resulting risk of infection is reduced.

This method moreover results in a great speed, which is particularly important when a large number of humans or animals must be injected.

This known method has the drawback that it is only suitable for injecting animals from a distance. This leads to dangerous situations, since the kinetic energy of a "fired" carrier is so great that it can easily cause serious injury.

Another drawback lies in the fact that the accuracy of the location at which the carrier enters the body is low, so that there is a great chance of the carrier entering the body at a less suitable position. Moreover, the kinetic energy of the carrier when it enters the body is strongly dependent on the distance between body and device. At a great distance there is indeed no longer any guarantee that the position of the carrier is still axial when it enters the body; the risk of injury is therefore great.

The invention therefore provides a method which is characterized in that during carrying of a rigid carrier into the body by means of gas pressure the device with which the carrier is carried into the body is held against the body.

Use is made herein of a device which is provided with a chamber in which a carrier containing the pharmaceutical preparation can be placed, a barrel connecting onto this chamber and means for carrying the carrier by means of gas pressure through the barrel into the body for injecting, characterized by means for blocking the use of the device when it is not pressed against a body.

It is noted here that it is known to introduce pharmaceutical preparations in the form of a carrier into the body, wherein in general these pharmaceutical preparations release their pharmaceutically active substance slowly. In this known method these carriers are arranged surgically in the body, which of course entails high costs. These surgically arranged carriers often leave behind a remnant which must be removed, once again surgically, or which result in the occurrence of abscesses or infections.

The present invention will be elucidated hereinbelow with reference to the annexed figures, in which:

FIG. 1 shows a partly broken away perspective view of a device according to the invention;

FIG. 2 shows a partly broken away detail view of the device depicted in FIG. 1;

FIG. 4 is a perspective view of a carrier for use in the method according to the invention.

Figure 3:
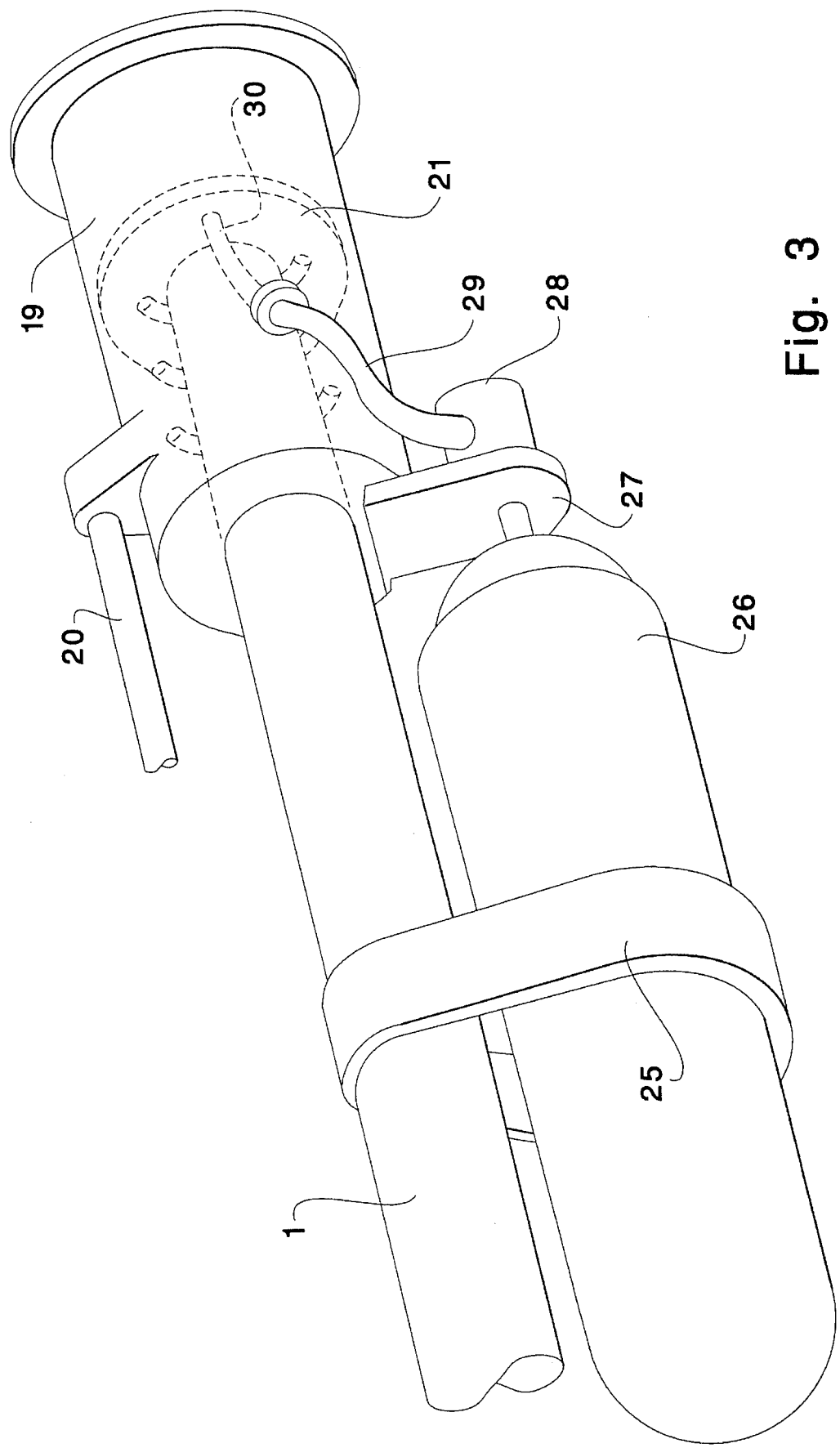
FIG. 3 is a detail view broken away in another manner of the device depicted in FIG. 1.

The device depicted in FIG. 1 is formed by a barrel 1 in which a chamber 2 is arranged. Situated under chamber 2 is magazine 3 in which a spring 4 is arranged for urging carriers 5 toward the chamber 2. It is also possible to feed the carriers on a belt or on a chain in the manner of a machine gun. Another possibility is formed by the use of an annular magazine in which the carriers are arranged. The side of chamber 2 remote from the barrel 1 is connected by means of a channel 6 to a pressure vessel 7. A closing valve 8 is arranged in channel 6. For handling of the thus formed release device 9 a first hand-grip 10 is fixed to the barrel 1 and a second hand-grip 11 to the channel 6. The closing valve 8 is further connected to a trigger 12. The hand-grips are preferably integrated into the housing.

As a result of the fact that the device is pressed with the barrel against the body for injecting, the required kinetic energy of the carrier is small so that the device with a pressure vessel 7 incorporated therein can inject a large number of carriers.

In order to charge the vessel 7 it is provided with a connection 13 in which can be arranged a reducing valve 14 in order to make adjustable the pressure with which the gases reach chamber 2 and to enable maintaining of this pressure at the adjusted value.

Further arranged on the front side of the barrel 1 is a sleeve 19 which is slidable in axial direction on the barrel 2. Sleeve 19 is connected by means of a rod 20 to the closing valve 8. This is a safety device; it is only possible to operate the trigger 12 when the sleeve 19 is pressed rearward in relation to the barrel 1, so that only when sleeve 19 has been shifted through contact with a body for injecting is it possible to pull the trigger 12 and cause a carrier to move through barrel 1 into the body for injecting.

The construction is shown in more detail in FIG. 2. Sleeve 19 is provided with an internal edge 21 with which guiding on the barrel 1 takes place. Further, a ring 22 is screwed on the rear end of sleeve 19, wherein ring 22 likewise provides guiding on the barrel. To prevent the sleeve 19 being removed from the barrel pins 23 are arranged on the barrel. Arranged between pins 23 and ring 21 is a coil spring ring 24 which ensures that sleeve 19 is retained in its extreme position. Only when the end of barrel 1 is pressed onto the skin of a body for injecting is the sleeve 19 moved rearward counter to the spring action of spring 24 so that the rod 20 is moved to the rear and the trigger 12 can be pulled.

For this purpose a pressure vessel in the form of an aerosol 26 is connected to the barrel 1 by means of a fastening element in the form of a belt 25. Further connected to sleeve 19 is a bracket 27 which rests against the head 28 of the aerosol 26.

Thus is created a mechanism wherein, when the sleeve is pressed in by the body for injecting, the aerosol is activated and a portion of the contents of aerosol 26 is atomized inside sleeve 19. For this purpose the head 28 of the aerosol is connected by means of a flexible hose 29 to the internal edge 21 of the sleeve, in which an opening 30 is arranged through which the hose 29 extends. The contents of the aerosol are formed by a liquid or a gas which has a disinfecting or marking action. In preference both properties are incorporated in the same liquid, for instance tincture of iodine, brilliant green or mercurochrome. It is of course possible to employ other liquids, for instance a mixture of a highly coloured liquid for marking and a liquid with a disinfecting action.

It will be apparent that there are other options for atomizing liquid, for instance a vessel which is pumped up at each stroke of the sleeve relative to the barrel. It is also possible to use the kinetic energy of the carrier to atomize the liquid, for instance by means of the suction occurring after passage of the carrier.

It is of course likewise possible, when the situation lends itself thereto, to make use of either a disinfecting liquid or a marking liquid.

It will be apparent that other embodiments of mechanisms for safety and spraying of marking and/or disinfecting liquid are possible; the above mentioned construction is only one embodiment.

Finally, FIG. 4 shows an embodiment of a carrier according to the present invention. The carrier designated in its entirety by 5 is formed by a substantially cylindrical body 30 which is provided on one side with a conical tip 31. The other side of the cylindrical body 30 is flattened. It will be apparent that this shape is suitable for firing as carrier into a body by means of the device depicted in FIG. 1, wherein penetration through the skin is facilitated by the conical shape.

It is also possible to apply other carrier shapes. Such a carrier can be manufactured entirely of a pharmaceutically active substance, although it is also possible that the quantity of pharmaceutically active substance is too small to produce such a carrier. In such a situation the carrier is manufactured from a mixture of pharmaceutically active substance and an additive material, or only an additive material with recesses for the pharmaceutically active substance. The additive is of course chosen herein such that the carrier has a sufficient mechanical strength.

It will be apparent that the dimensions of the carrier are subject to the field of application; in human applications a length of several millimetres is envisaged in the first instance. In veterinary applications the dimensions depend of course on the type of animal for injecting; in the case of pigs or cows is envisaged a carrier with a length of about 1 cm and a diameter of about 2–3 mm.

It is likewise possible to provide the carrier with a cavity 32 and to arrange the pharmaceutically active substance in this cavity.

It is possible to embody the carrier as capsule or to use a sponge-like structure of robust bio-degradable material, in the cavities of which is arranged pharmaceutically active substance.

It is also possible to embody for instance only the tip in a robust bio-degradable material.

It is otherwise possible to select the material of the carrier such that the pharmaceutically active substance is absorbed into the body immediately after injecting. It is also possible that the pharmaceutically active substance is only released slowly.

Use can be made herein of coatings applied round the active substance. It is even possible to use different units of pharmaceutically active substances with different coatings so that the pharmaceutically active substances are released as it were in stages after different periods of time, for instance in the case of different pharmaceutically active substances.

It is attractive to embody the carrier such that it disappears within a determined time, for instance several weeks or even within several hours. In order to achieve this the carrier must consist not only of the pharmaceutically active substance but also of rapidly bio-degradable material. Use is preferably made herein of starch or of mainly starch-containing substances. These are given a form-retaining shape, for instance by injection moulding.

It is of course possible to administer such a rigid carrier in other manner, for instance by means of an operation of other usual means of application.

The above embodiment is suitable for successive injecting with the same pharmaceutical preparation. Other embodiments are conceivable which are suitable for successive injecting with different preparations and which are provided for this purpose with a magazine in which only one carrier can be placed. It is even possible to use the present invention to inject chips into animals. Herein the chips can be injected directly when they have a suitable form, but they can also be arranged in a carrier of bio-degradable material.

I claim:

1. Method for injecting humans and animals with a pharmaceutical preparation, wherein the preparation is held in a rigid carrier and wherein the carrier is carried through the skin into the body by means of gas pressure, characterized in that during carrying of the rigid carrier into the body by means of gas pressure the device with which the carrier is carried into the body is held against the body.

2. Method as claimed in claim 1, characterized in that the carrier is carried into the body by means of compressed air.

3. Method as claimed in claim 1, characterized in that in one operation with the injecting the area of the skin where the injection takes place is disinfected.

4. Method as claimed in claim 1, characterized in that in one operation with the injecting the animal for injecting is marked.

5. Device for injecting animals or humans with a pharmaceutical preparation, comprising a chamber into which a carrier containing the pharmaceutical preparation can be introduced, a barrel connecting onto this chamber, means for carrying the carrier by means of gas pressure through the barrel into the body for injecting, and means for initiating release of the gas pressure into the barrel, characterized by means for blocking the use of the device when it is not pressed against a body.

6. Device as claimed in claim 5, characterized in that the means of generating the gas pressure are formed by a vessel for filling with compressed gas which is connected to the chamber by means of a closing valve.

7. Device as claimed in claim 5, characterized in that on one of its sides the device contains a handle-grip, and on its other side it containes the aperture from which the carrier emerges.

8. Device as claimed in claim 5, characterized in that at the end of the barrel a member is arranged, which when the end of the barrel is pressed onto the skin, atomizes a liquid, for instance a disinfecting liquid or a highly coloured liquid onto the skin.

9. Device as claimed in claim 5, characterized by a magazine for the carrier, wherein means are arranged in the magazine for urging the carriers into the chamber.

10. Carrier fit for injection by an apparatus according to one of claims 5–9, characterized in that said carrier comprises a bio-degradable substance and a pharmaceutically active substance.

11. Carrier as claimed in claim 10, characterized in that the carrier comprises a pharmaceutically active substance an a bio-degradable substance.

12. Carrier as claimed in claim 10, characterized in that the carrier is formed such that the pharmaceutically active substance is released slowly from the carrier.

13. Carrier as claimed in claim 10, characterized in that the carrier is formed by a rigid hollow shell and that in the shell there is a space for arranging the pharmaceutically active substance.

14. Carrier as claimed in claim 10, characterized in that the rigid carrier contains mainly starch.

15. Carrier as claimed in claim 14, characterized in that the carrier is manufactured by injection moulding.

16. Carrier suitable for injection by an apparatus according to one of claims 5–9, characterized in that the carrier contains an identifiable element, for instance a chip.

* * * * *